United States Patent [19]

Mostafa

[11] Patent Number: 4,776,881
[45] Date of Patent: Oct. 11, 1988

[54] HERBICIDE COMPOSITION AND PROCESS

[75] Inventor: Mohamed A. Mostafa, Walnut Creek, Calif.

[73] Assignee: Stauffer Chemical Co., Westport, Conn.

[21] Appl. No.: 881,320

[22] Filed: Jul. 1, 1986

[51] Int. Cl.$^4$ .............................................. A01N 25/00
[52] U.S. Cl. .................................... 71/95; 71/DIG. 1
[58] Field of Search .............................. 71/95, DIG. 1

[56] References Cited

U.S. PATENT DOCUMENTS

| | | | |
|---|---|---|---|
| 2,531,429 | 11/1950 | Hauser | 260/448 |
| 2,966,506 | 12/1960 | Jordan | 260/448 |
| 4,110,105 | 8/1978 | Teach | 71/95 |

Primary Examiner—Catherine L. Mills
Attorney, Agent, or Firm—Michael J. Bradley; Paul R. Martin

[57] ABSTRACT

An improved herbicide composition comprising: (a) from about 10 to about 60 percent 1-m-trifluoromethyl-phenyl-3-chloro-4-chloromethyl-2-pyrrolidone; (b) from about 1 to about 10 percent aluminum oxide/magnesium oxide wherein the mole ratio of aluminum oxide to magnesium oxide ranges from about 1:1 to about 1:2, or a polyamide; (c) from about 5 to about 15 percent high surface area silica; (d) from about 15 to about 40 percent amine treated bentonite; (e) from about 1 to about 10 percent dispersant; (f) from about 1 to about 10 percent wetting agent; and (g) from about 1 to about 10 percent urea.

16 Claims, No Drawings

HERBICIDE COMPOSITION AND PROCESS

BACKGROUND OF THE INVENTION

This invention is concerned with an improved herbicide composition of the wettable powder or dry flowable type and a process for making it.

Chemical herbicide compositions which are effective against a variety of weed species are conventionally formulated either as aqueous solutions, emulsifiable concentrates, dusts or granular particles.

Subspecies of the dust and granular particle type formulations are formulations which are designated as wettable powder or dry flowable formulations. Wettable powders or dry flowable formulations are dry compositions which are intended to be suspended as slurries and sprayed on the target, using well known techniques. These powders generally contain from about 20 to about 95% by weight active pesticide ingredient, up to about 80% by weight dispersible and/or soluble inert diluents such as clays vermiculite, carbon black, and the like, and from about 1 to about 10% by weight of surfactants and dispersants for promoting rapid wetting and dispersing water and disperability in the spray tanks. Wettable powder formulations or dry flowable formulations are normally prepared by incorporating the active herbicide or pesticide with the diluent carriers which absorb the active ingredients, and then the diluent carriers with the absorbed active ingredients are hammer milled to produce powders of the granule size desired.

There are a number of problems associated with the preparation of a wettable powder or dry flowable formulation. Specifically, it is not always possible to mill the active ingredient absorbed onto the diluent carrier to the optimum size. In addition, the inclusion of a dispersant in the formulation sometimes competes with the absorption process between the active ingredients and the carrier. Further, some dispersants or emulsifiers which are used are toxic to humans or animals with which they come into contact and require warning labels to be applied to the product which restricts the breadth of use possible.

THE PRIOR ART

A chemical compound which is intended for use in various formulations as the active ingredient in herbicidal compositions is 1-m-trifluoromethylphenyl-3-chloro-4-chloromethyl-2-pyrrolidone. This compound and others of the same type are described and claimed in U.S. Pat. No. 4,110,105.

A particular problem occurs in making wettable powders or dry flowables when the active ingredient is a pyrrolidone of the type described in U.S. Pat. No. 4,110,105, which relates to the difficulty in making the active ingredient. The "technical" product is a low-melting solid with a wide melting range of 43°-71° C. containing various impurities. When produced by conventional techniques, the pyrrolidone solidifies into a solid chunk, making it necessary to chip out and break up the compound in order that it might be milled and various additives combined therewith. It has been found to be virtually impossible to manufacture the pyrrolidone active ingredient such that the particle size is comparable with other ingredients for wettable powder and dry flowable compositions. The heat generated during milling is sufficient to soften and partially melt the low melting constituents of the technical. This, in turn, causes blocking of the screen off the mill, preventing completion of the process.

An additional problem which has been observed in connection with the use of this herbicide in wettable powder and dry flowable formulations is that the active ingredient does not maintain its suspensibility after storage, and the dispersant/wetting agent which is often used in conjunction with the formulation of this compound is a potential source of eye damage and requires restricted use conditions by the applicator or others handling the herbicide.

As used herein, the term "wettable powder" refers to a composition comprising the technical herbicide plus the carrier and other additives in powder form.

The term "dry flowable" to a composition comprising the technical herbicide in powder form, together with other inert carriers and additives, which has been agglomerated to a particular particle size by wetting action.

The term "herbicide" is used herein to denote a compound which controls or modifies the growth of plants. The term "herbicidally effective amount" is used to indicate the quantity of such a compound or combination of such compounds which is capable of producing a controlling or modifying effect. Controlling or modifying effects include all deviations from natural development, for example: killing, retardation, leaf burn, dwarfing and the like. The term "plants" is used to include all post-emergent vegetation, ranging from seedlings to established vegetation.

DESCRIPTION OF THE INVENTION

It has now been found that a herbicide composition using as the active ingredient 1-m-trifluoromethylphenyl-3-chloro-4-chloromethyl-2-pyrrolidone or similar pyrrolidones can be formulated by using a mixture of components which provides a composition having improved millability, good suspensibility after storage and reduced eye irritation.

The herbicidal composition of this invention comprises:

(a) from about 10 to about 60 percent by weight of a herbicidally effective amount of a monocyclic aromatic N-substituted halo-2-pyrrolidone having the formula

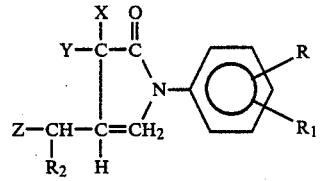

in which X is hydrogen, chlorine or methyl; Y is hydrogen, chlorine or bromine, Z is chlorine or bromine; $R_2$ is alkyl having from 1 to 4 carbon atoms, inclusive or hydrogen; R is hydrogen, alkyl having from 1 to 4 carbon atoms, inclusive, acetyl, chlorine, bromine, fluorine, iodine, trifluoromethyl, nitro, cyano, alkoxy having from 1 to 4 carbon atoms, inclusive, alkylthio having from 1 to 4 carbon atoms, inclusive, alkylsulfinyl having from 1 to 4 carbon atoms, inclusive, alkylsulfonyl having from 1 to 4 carbon atoms, inclusive, trifluoromethylthio, trifluoromethylsulfinyl, trifluoromethylsulfonyl, pentafluoropropionamido, or 3-methylureido; and $R_1$ is hydrogen, alkyl having from 1 to 4 carbon atoms, inclusive, chlorine or trifluoromethyl, which has been conditioned with a mixture of about 1 to about 10 percent of weight of aluminum oxide/magnesium oxide wherein the mole ratio of aluminum oxide to magnesium oxide ranges from about 1:1 to about 1:2, or a polyamide;

(b) from about 5 to about 15 percent by weight of a high surface area silica;

(c) from about 15 to about 40 percent by weight of an amine treated bentonite clay;

(d) from about 1 to about 10 percent by weight of a nonionic dispersant;

(e) from about 1 to about 10 percent by weight of an anionic wetting agent; and (f) from about 1 to about 10 percent by weight urea.

Unless otherwise indicated herein, all weight percentages refer to weight percent of the entire composition.

The process of the invention comprises those steps used in the production of the herbicidal composition of the invention. The process comprises the steps of:

(a) melting a quantity of a solid technical pyrrolidone herbicide having the formula

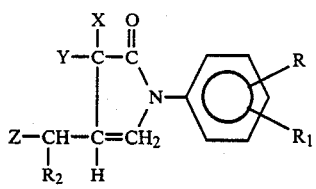

in which X is hydrogen, chlorine or methyl; Y is hydrogen, chlorine or bromine, Z is chlorine or bromine; $R_2$ is alkyl having from 1 to 4 carbon atoms, inclusive or hydrogen; R is hydrogen, alkyl having from 1 to 4 carbon atoms, inclusive, acetyl, chlorine, bromine, fluorine, iodine, trifluoromethyl, nitro, cyano, alkoxy having from 1 to 4 carbon atoms, inclusive, alkylthio having from 1 to 4 carbon atoms, inclusive, alkylsulfinyl having from 1 to 4 carbon atoms, inclusive, alkylsulfonyl having from 1 to 4 carbon atoms, inclusive, trifluoromethylthio, trifluoromethylsulfinyl, trifluromethylsulfonyl, pentafluoroproprionamido, or 3-methylureido; and $R_1$ is hydrogen, alkyl having from 1 to 4 carbon atoms, inclusive, chlorine or trifluoromethyl;

(b) admixing with said melted technical pyrrolidone herbicide from about 1 to about 10 percent by weight of aluminum oxide/magnesium oxide wherein the mole ratio of aluminum oxide to magnesium oxide ranges from about 1:1 to about 1:2, or a polyamide;

(c) admixing with the mixture formed in (b) above from about 5 to about 15 weight percent of a high surface area silica;

(d) hardening said mixture formed in (c) above and subsequently communiting and milling said mixture until a powder of a desired particle size is obtained;

(e) admixing with said powder formed in (d) from about 15 to about 40 percent by weight of an acidic bentonite clay which has been treated with an amine so as to modify the surface characteristics thereof;

(f) blending said clay with said powder in a milling device for a sufficient period of time to achieve adequate adsorption of the powder onto said clay;

(g) adding to said mixture of powder and clay in the milling device from about 1 to about 10 percent by weight of a nonionic dispersant, from about 1 to 10 percent by weight of an anionic wetting agent, from about 1 to about 10 percent by weight weight urea, and continuing to mill said mixture to obtain a wettable powder of the desired particle size.

Additional additives such as binders can also be incorporated into the composition at any stage, if desired.

The dry flowable formulation produced in accordance with the process of this invention is produced by the additional step (g) of clumping said wettable powder to a specific granule size by spraying water thereon and drying to yield a powder having a moisture content of not more than about 0.5 percent by weight. The drying is conventionally carried out on a fluidized bed.

The product produced in accordance with this process is more easily milled to the desired particle size than has previously been the case, has good suspensibility and is substantially less irritable to the eyes than previous prior art formulations because of the dispersant/wetting agent combination used.

Wettable powders conventionally have a particle size ranging from about 6 to about 8 microns.

As used herein, the term "conditioned" refers to the physical incorporation of the oxides or polyamide with the pyrrolidone active ingredient.

In the process and compositions of the invention, the pyrrolidone technical is treated with a mixture of aluminum oxide/magnesium oxide or a polyamide to enhance the absorbability of the technical onto the carrier (clay) via acid-base interactions and to improve the millibility of the product by decreasing or narrowing the melting range of the technical.

Preferably, the mole ratio of aluminum oxide to magnesium oxide is 1:1, but ratios of up to 1:2 would also be acceptable. The oxides are normally incorporated as powders of about 60 mesh.

Under normal circumstances, the pyrrolidone technical, which is produced by conventional techniques, has up to about 10% impurities. This results in the technical having a melting range of about 43° to 71° C. As the purity increases, the melting range diminishes.

It is not known exactly why the addition of the aluminum oxide/magnesium oxide or polyamide has the effect of decreasing or narrowing the melting range of the technical. That is does, however, is beneficial to the overall composition for the reason that it enables the technical to be more easily milled and enhances the adsorption of the technical onto the carrier.

It is thought that an acid-base interaction is generated between the basic (electron donor), oxygen on the 1-m-trifluoromethylphenyl-3-chloro-4-chloromethyl-2-pyrrolidone molecules with either the acidic positively charged (electron acceptor) $Al^{+++}$ and $Mg^{++}$ of the oxides or via a hydrogen bonding in the case of the amide.

These interactions can be illustrated as follows:

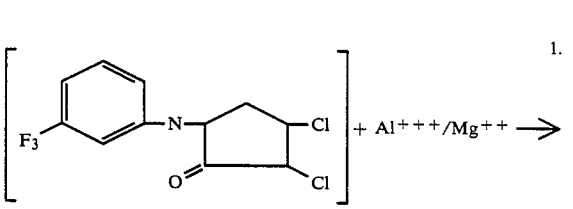

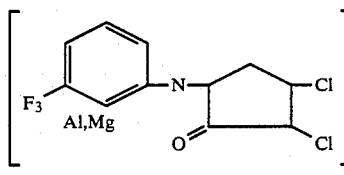

or

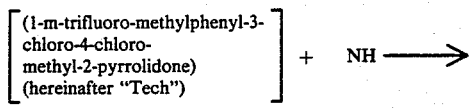

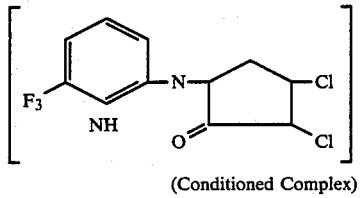

(Conditioned Complex)

The acid-base interactions appear to result in a superior milling process for the 1-m-trifluoromethylphenyl-3-chloro-4-chloromethyl-2-pyrrolidone technical without any softening or melting during any stage of the process.

The preferred amide for use in the invention is Witcoamide-70, a polyamide sold by Witco Chemical Company.

Witcoamide-70 is a monoethanol amine stearamide, wherein the alkyl group has 18 carbon atoms. Similar amides where the alkyl group ranges from 12 to 20 carbon atoms in length would also be suitable.

The preferred pyrrolidone compound for use in the compositions and process of the invention is 1-m-trifluoromethylphenyl-3-chloro-4-chloromoethyl-2-pyrrolidone. As previously indicated, this compound is described and claimed in U.S. Pat. No. 4,110,105, along with a disclosure of the method of manufacture thereof.

Mixing the pre-conditioned pyrrolidone technical with the high surface area silica is carried out to generate the technical complex species consisting of pyrrolidone technical/oxides/silica combination with predominant acidic sites, which is more easily millable.

As used herein, the term "high surface area silica" refers to a silica having a surface area of from about 80 to about 600 g/m².

The preferred high surface area silica for use in the compositions and process of this invention is a silica sold under the trade name Hi-Sil ®, which has a surface area of 120 g/m² and is sold by PPG Company. Other high surface area silicas can also be used.

To the conditioned pyrrolidone tech complex, the Hi-Sil ® is added. By mixing the acidic Hi-Sil ® with the melt complex, a predominantly acidic species is generated by adsorption process of the technical onto the Hi-Sil ®. The new species now exists consisting of 1-m-trifluoromethylphenyl-3-chloro-4-chloromethyl-2-pyrrolidone/oxides/Hi-Sil ®.

The clay carrier (bentonite clay) is modified by spraying the surface thereof and admixing with it from about 3 to about 6 percent by weight of an amine, preferably triethylamine for a period of about 45 minutes. The purpose of this is to convert the clay which normally carries acidic functional groups to one having predominantly basic sites. While triethylamine is preferred for this purpose, other primary, secondary or tertiary amines can also be used.

The preferred clay carrier for use in the compositions and process of the invention is Type 41 clay obtained from the Southern Clay Co.

Type 41 clay is a kaolinite clay. Kaolinite has a crystal structure of 2 layers sheet with a plate particle shape. The surface of the plate is negatively charged while the edge (AlOH) group is positively charged.

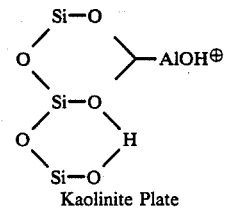

Kaolinite Plate

Surface characterization of kaolinite reveals a strongly acidic nature (Indicator dyes pK<4.8). The acidity of kaolinite is attributed to the AlOH groups.

These acidic sites of Type 41 clay will not promote an effective adsorption of the predominantly acidic conditioned pyrrolidone herbicide. So the acidic sites on the clay are modified by treating the clay with triethylamine (TEA) or other amine. This treatment renders Type 41 clay to have predominantly basic surface sites (pKa>4.8). An acid-base interaction is now promoted between the acidic-conditioned technical and the basic-modified clay. A two-step illustration of these interactions is:

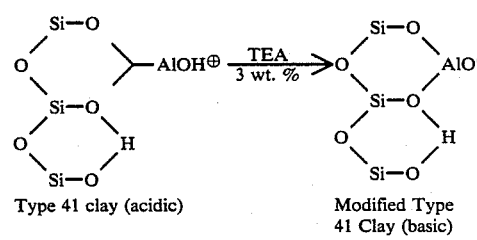

Type 41 clay (acidic)    Modified Type 41 Clay (basic)    I.

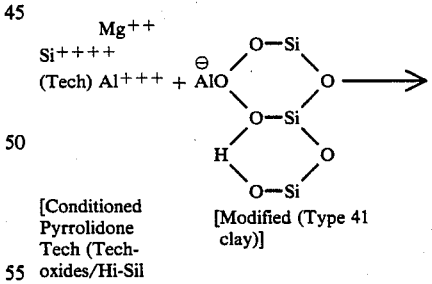

[Conditioned Pyrrolidone Tech (Tech-oxides/Hi-Sil complex)]    [Modified (Type 41 clay)]    II.

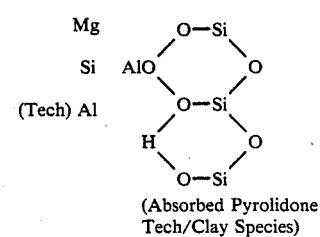

(Absorbed Pyrolidone Tech/Clay Species)

The dispersant/wetting agent couple has a 3-fold function. First, the dispersant does not compete with the adsorption process between the predominantly acidic conditioned technical and the predominantly basic modified clay carrier. Second, the dispersant acts as a protective coating to the new matrix of (technical pyrrolidone/oxides/silica/clay). Third, the dispersant/wetting agent combination is not irritable to the eyes or other tissues.

It has been found that a combination of Pluraflo® D-1, an ethylene oxide/propylene oxide block copolymer sold by BASF Corporation., and sodium dodecylbenzene sulfonate, a surfactant commonly available (Stepan Chemical Co.), is most suitable for the intended purpose.

The nonionic Pluraflo D-1 fulfills all the three requirements for its functions. Being a nonionic, Pluraflo does not interfere competitively with the adsorption process between the conditioned pyrrolidone technical and the modified clay. It also provides a protective coating around the 1-m-trifluoromethylphenyl-3-chloro-4-chloromethyl-2-pyrrolidone/clay species.

Other surfactants can be used instead of the sodium dodecylbenzene sulfonate, the criteria being that the surfactant must be one which has the ability to lower the surface tension of the suspension ultimely produced.

Sodium dodocylbenzene sulfonate added to the formulation reduces the surface energy of dispersing medium, $H_2O$. But, it does not interfere with the interfacial interactions of the dispersant with the technical/clay species.

The purpose of incorporating urea into the formulation is to insure the overall basicity of the medium or dispersion and thus minimize any reversible adsorption which might occur between the technical and the clay. Such desorption process would lead to a formulation having poor suspensibility.

By "suspensibility" is meant the ability to maintain finely divided particles evenly dispersed or suspended in the liquid formulation in which the powders are ultimately dispersed.

Incorporation of urea in the formulation provides the extra step to ensure the overall basicity conditions for the wettable powder and dry flowable. This maintains a good suspensibility of the product after storing at 110° F., up to a period of 12 weeks.

The good suspensibility obtained from these new formulations is the result of a steric stabilization and/or an electrostatic repulsion between the new formed species of the conditioned (1-m-trifluoromethylphenyl-3-chloro-4-chloromethyl-2-pyrrolidone), Hi-Sil ® and the modified clay and dispersant.

The need for all and each of the ingredients of the formulation is demonstrated. Wettable powder and dry flowable formulations prepared without conditioned technical, modified clay or urea proved to have a lower initial suspensibility. This evidence supports the model of the acid-base interaction via adsorption of the conditioned technical onto the modified clay.

A further support of this model and the need for basic medium around the 1-m-trifluoromethylphenyl-3-chloro-4-chloromethyl-2-pyrrolidone or other pyrrolidone is demonstrated by granulating the 1-m-trifluoromethylphenyl-3-chloro-4-chloromethyl-2-pyrrolidone with acidic polymer solution. Over 40% loss of the initial suspensibility of 1-m-trifluoromethylphenyl-3-chloro-4-chloromethyl-2-pyrrolidone is observed when 2% of the acidic PVA (polyvinyl alcohol) solution is used for granulation rather than tap water or basic (high pH) water.

Granulating the 1-m-trifluoromethylphenyl-3-chloro-4-chloromethyl-2-pyrrolidone wettable powder with mixtures of nonionic dispersant/wetting agent (1:1) like Iconol WA-1/Iconol DDP 10.5 or Span 85/Iconol DDP 10.5, does not allow for any further or different improvement in CIPAC suspensibility of 1-m-trifluoromethylphenyl-3-chloro-4-chloromethyl-2-pyrrolidone.

The process of the invention will be more easily understood by reference to the following examples.

EXAMPLE 1

Ten pounds of solid technical 1-m-trifluoromethylphenyl-3-chloro-4-chloromethyl-2-pyrrolidone was obtained, placed in a container and melted over a period of several hours. Following this, 0.3 pounds of a 1:1 mixture of aluminum oxide and magnesium oxide was blended with the melted technical for a period of 0.5 hour. Thereafter, 1.1 pounds of Hi-Sil ®, a high surface area silica, was added to the technical/oxide blend, and mixing was continued for an additional 0.5 hour.

Thereafter, the technical pyrrolidone plus blended materials was allowed to harden. 9.44 pounds of this material was chipped out and placed in a hammer mill. Thereafter, 4.05 pounds of Type 41 clay which had been previously treated with 3% triethylamine with respect to the clay was added to the hammer mill and milling was continued for approximately one hour. At this time, 0.53 pound of Pluraflo ® D-1, 0.38 pound of sodium dodecylbenzene sulfonate plus 0.60 pounds of urea was added to the hammer mill and milling was continued for an additional hour.

The wettable powder thus formed was removed from the hammer mill and placed in an air mill and further reduced in size until a powder of approximately 6 micron particle size was obtained.

At the end of that time, the wettable powder was removed from the air mill and converted into a dry flowable by granulating into a Ferro-Tech 16 inch pan. The granulation process is attained by spraying the wettable powder with water as a binder solution. This is followed by a drying process on a fluidized bed until a moisture content of 0.10% or less is obtained.

EXAMPLE 2

Ten pounds of solid technical 1-m-trifluoromethylphenyl-3-chloro-4-chloromethyl-2-pyrrolidone was obtained, placed in a container and melted over a period of several hours. Following this, 0.3 pounds of polyamide (Witcoamide-70) was blended with the melted technical for a period of 0.5 hour. Thereafter, 1.1 pounds of Hi-Sil ®, a high surface area silica, was added to the technical/oxide blend, and mixing was continued for an additional 0.5 hour.

Thereafter, the technical pyrrolidone plus blended materials was allowed to harden. 9.44 pounds of this material was chipped out and placed in a hammer mill. Thereafter, 4.05 pounds of Type 41 clay which had been previously treated with 3% triethylamine was added to the hammer mill and milling was continued for approximately 1 hour. At this time, 0.53 pound of Pluraflo ® D-1, 0.38 pound of sodium dodecylbenzyl sulfonate plus 0.60 pounds of urea was added to the hammer mill and milling was continued for an additional hour.

The wettable powder thus formed was then removed from the hammer mill and placed in an air mill and further reduced in size until a powder of approximately 6 micron particle size was obtained.

At the end of that time, the wettable powder was removed from the air mill and converted into a dry flowable by granulating (Ferro-Tech 16" Pan) with water and then drying on a fluidized bed until a moisture content of 0.10% was obtained.

The improved characteristics of the herbicide compositions of this invention produced in accordance with the process described herein is demonstrated in the following example.

EXAMPLE 3

In this example, a wettable powder (WP) having the formulation set forth in Example 4 wherein the pyrrolidone technical compound was conditioned with either Witco ® amide 70 or an aluminum oxide/magnesium oxide mixture had its suspensibility measured and compared with dry flowable (DF) formulations having essentially the same overall composition, but which had been granulatd with several media as indicated.

In comparing the results of the suspensibility tests, it can been seen that a dry flowable formulation requires a neutral or a basic medium (Exp. 1, 2 and 3) in order to have good suspensibility. A dry flowable formulation wherein the granulating medium is an acidic medium such as polyvinyl alcohol (Exp. 6) showed substantially less effective suspensibility than comparable formulations which had been granulated in a neutral or a basic medium.

The various formulations were tested with respect to their suspensibility in accordance with the procedure described in CIPAC Handbook, Vol. I, p. 861 (1970), published by CIPAC Limited, Hertfordshire, England.

The results of these tests are set forth in Table 1 below.

TABLE 1

Wettable powder and dry flowable Studies - CIPAC Suspensibility (%)

| Exp. # | Granulating Medium | Tech prep'd w/Witcoamide 70 | | Tech prep'd w/Al2O3/MgO | |
|---|---|---|---|---|---|
| | | Initial | 1 Wk/ 110° F. | Initial | 1 wk/ 110° F. |
| 1 | WP — | 98 | 70 | 95 | 82 |
| 2 | DF H2O | 75 | 59 | 80 | 71 |
| 3 | DF pH 11.8 H2O | 80 | 63 | 82 | 65 |
| 4 | DF Iconol WA-1/ DDP 10.5 (2%) | 76 | 64 | 72 | 66 |
| 5 | DF Span 85/DDP 10.5 (2%) | 76 | 60 | 60 | 47 |
| 6 | DF PVA (2%) | 45 | 40 | 60 | 45 |

WP = wettable powder
DF = dry flowable

Preferred ranges for the various ingredients incorporated in the compositions of this invention are as follows:

(a) from about 10 to about 60 percent pyrrolidone;

(b) from about 1 to about 10 percent aluminum oxide/magnesium oxide (1:1) or polyamide;

(c) from about 5 to about 15 percent Hi-Sil ®;

(d) from about 15 to about 40 percent amine treated Type 41 clay;

(e) from about 1 to about 10 percent dispersant (f) from about 1 to about 10 percent wetting agent; and (g) from about 1 to about 10 percent urea.

Representative formulations of the herbicide composition of this invention are as follows.

EXAMPLE 4

| Ingredients | Wt. % |
|---|---|
| 1-m-trifluoromethylphenyl-3-chloro-4-chloromethyl-2-pyrrolidone 92.3% (100%) | 55.20 (50.90) |
| aluminum oxide/magnesium oxide (1:1) | 1.63 |
| Hi-Sil ® | 6.15 |
| amine treated Type 41 clay | 27.02 |
| Pluraflo D-1 | 3.50 |
| sodium dodecyl benzene sulfonate | 2.50 |
| Urea | 4.00 |
| | 100.00 |

EXAMPLE 5

| Ingredients | Wt. % |
|---|---|
| 1-m-trifluoromethylphenyl-3-chloro-4-chloromethyl-2-pyrrolidone 92.3% | 55.20 (50.90) |
| Witcoamide 70 | 1.63 |
| Hi-Sil ® | 6.15 |
| amine treated Type 41 clay | 27.02 |
| Pluraflo D-1 | 3.50 |
| sodium dodecyl benzene sulfonate | 2.50 |
| Urea | 4.00 |
| | 100.00 |

While the herbicide compositions of this invention are most effective in terms of increased suspensibility and improved millability, when the pre-conditioned pyrrolidone, the high surface area silica, the amine-treated bentonite clay and the urea area all utilized as ingredients, commercially acceptable compositions in terms of suspensibility can also be obtained when one or more of the aforementioned ingredients is not utilized in the most desired form. That is, for example, if the technical pyrrolidone is utilized which has not been treated with the aforementioned aluminum/magnesium oxide combination, or the polyamide, a satisfactory composition can still be achieved. Similarly, commercially acceptable formulations are obtained when nonamine-treated type 41 clay is utilized, or when the urea is omitted.

Thus, it is contemplated that the compositions of this invention also encompass those formulations wherein one or more of the constituents, i.e., pyrrolidone or bentonite clay, are present in the untreated form, or, in the case of urea, are omitted.

Representative formulations embodying these aspects of the invention are set forth below.

EXAMPLE 6

| Ingredients | Wt. % |
|---|---|
| 1-m-trifluoromethylphenyl-3-chloro-4-chloromethyl-2-pyrrolidone 92.3% | 55.20 (50.90) |
| aluminum oxide/magnesium oxide (1:1) | 0.0 |
| Hi-Sil ® | 6.15 |
| treated Type 41 clay | 28.65 |
| Pluraflo D-1 | 3.50 |
| sodium dodecyl benzene sulfonate | 2.50 |
| Urea | 4.0 |
| | 100.00 |

EXAMPLE 7 hz,1/32

| Ingredients | Wt. % | |
|---|---|---|
| 1-m-trifluoromethylphenyl-3-chloro-4-chloromethyl-2-pyrrolidone 92.3% | 55.20 | (50.90) |
| aluminum oxide/magnesium oxide (1:1) | 1.63 | |
| Hi-Sil ® | 6.15 | |
| untreated Type 41 clay | 27.02 | |
| Pluraflo D-1 | 3.50 | |
| sodium dodecyl benzene sulfonate | 2.50 | |
| Urea | 4.00 | |
| | 100.00 | |

EXAMPLE 8

| Ingredients | Wt. % | |
|---|---|---|
| 1-m-trifluoromethylphenyl-3-chloro-4-chloromethyl-2-pyrrolidone 92.3% | 55.20 | (50.90) |
| aluminum oxide/magnesium oxide (1:1) | 1.63 | |
| Hi-Sil ® | 6.15 | |
| treated Type 41 clay | 31.02 | |
| Pluraflo D-1 | 3.5 | |
| sodium dodecyl benzene sulfonate | 2.50 | |
| Urea | .00 | |
| | 100.00 | |

Other conventional additives can be incorporated into the compositions of the invention, as will be apparent to those skilled in art.

What is claimed is:

1. An improved herbicide composition comprising:
   (a) from about 10 to about 60 percent by weight of an herbicidally effective amount of a monocyclic aromatic N-substituted halo-2-pyrrolidone having the formula

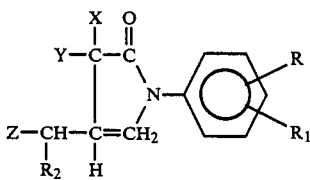

in which X is hydrogen, chlorine or methyl; Y is hydrogen, chlorine or bromine, Z is chlorine or bromine; $R_2$ is alkyl having from 1 to 4 carbon atoms, inclusive or hydrogen; R is hydrogen, alkyl having from 1 to 4 carbon atoms, inclusive, acetyl, chlorine, bromine, fluorine, iodine, trifluoromethyl, nitro, cyano, alkoxy having from 1 to 4 carbon atoms, inclusive, alkylthio having from 1 to 4 carbon atoms, inclusive, alkylsulfinyl having from 1 to 4 carbon atoms, inclusive, alkylsulfonyl having from 1 to 4 carbon atoms, inclusive, trifluoromethylthio, trifluoromethylsulfinyl, trifluromethylsulfonyl, pentafluoropropionamido, or 3-methylureido; and $R_1$ is hydrogen, alkyl having from 1 to 4 carbon atoms, inclusive, chlorine or trifluoromethyl, which pyrrolidone has been conditioned with a mixture of from about 1 to about 10 percent by weight of aluminum oxide/magnesium oxide where the mole ratio of aluminum oxide to magnesium oxide ranges from about 1:1 to about 1:2, or a polyamide;
   (b) from about 5 to about 15 percent by weight of a high surface area silica;
   (c) from about 15 to about 40 percent by weight of an amine treated bentonite clay;
   (d) from about 1 to about 10 percent by weight of a mixture of a nonionic dispersant;
   (e) from about 1 to 10 percent by weight of an anionic wetting agent; and
   (f) from about 1 to about 10 percent by weight urea.

2. The composition of claim 1 wherein said pyrrolidone is 1-m-trifluoromethylphenyl-3-chloro-4-chloromethyl-2-pyrrolidone.

3. The composition of claim 1 wherein said amine-treated bentonite clay is a type 41 bentonite clay which has been treated with triethylamine.

4. The composition of claim 1 wherein said high-surface area silica has a surface area of about 120 g/m².

5. The composition of claim 1 wherein said dispersant is an ethylene oxide/propylene oxide block copolymer.

6. The composition of claim 1 wherein said wetting agent is sodium dodecyl benzene sulfonate.

7. The composition of claim 1 wherein the mole ratio of aluminum oxide to magnesium oxide is 1:1.

8. The process of preparing an improved herbicide composition which comprises the steps of
   (a) melting a quantity of a technical pyrrolidone herbicide having the formula

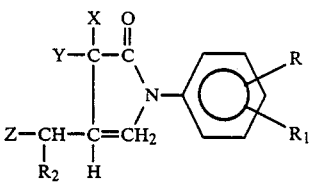

in which X is hydrogen, chlorine or methyl; Y is hydrogen, chlorine or bromine, Z is chlorine or bromine; $R_2$ is alkyl having from 1 to 4 carbon atoms, inclusive or hydrogen; R is hydrogen, alkyl having from 1 to 4 carbon atoms, inclusive, acetyl, chlorine, bromine, fluorine, iodine, trifluoromethyl, nitro, cyano, alkoxy having from 1 to 4 carbon atoms, inclusive, alkylthio having from 1 to 4 carbon atoms, inclusive, alkylsulfinyl having from 1 to 4 carbon atoms, inclusive, alkylsulfonyl having from 1 tone 4 carbon atoms, inclusive, trifluoromethylthio, trifluoromethylsulfinyl, trifluromethylsulfonyl, pentafluoropropionamido, or 3-methylureido; and $R_1$ is hydrogen, alkyl having from 1 to 4 carbon atoms, inclusive, chlori or trifluoromethyl;
   (b) admixing with said melted technical herbicide from about 1 to about 10 percent by weight of aluminum oxide/magnesium oxide wherein the mole ratio of aluminum oxide to magnesium oxide ranges from about 1:1 to about 1:2, or a polyamide;
   (c) admixing with the mixture formed in (b) above from about 5 to about 15 weight percent of a high surface area silica;
   (d) hardening said mixture formed in (c) above and subsequently communiting and milling said mixture until a powder of a desired particle size is obtained;
   (e) admixing with said powder formed in (d) from about 15 to about 40 percent by weight of an acidic bentonite clay which has been treated with an amine so as to modify the surface characteristics thereof;

(f) blending said clay with said powder in a milling device for a sufficient period of time to achieve adequate adsorption of the powder onto said clay;

(g) adding to said mixture of powder and clay in the milling device from about 1 to about 10 percent by weight of a nonionic dispersant, from about 1 to 10 percent by weight of an anionic wetting agent, from about 1 to about 10 percent by weight weight urea, and continuing to mill said mixture to obtain a wettable powder of the desired particle size.

9. The process of claim 8 wherein said high surface area silica has a surface area of about 160 g/m$^2$.

10. The process of claim 8 wherein said pryrolidone is 1-m-trifluoromethylphenyl-3-chloro-4-chloromethyl-2-pyrrolidone.

11. The process of claim 8 wherein said bentonite clay is a triethylamine-treated type 41 bentonite clay.

12. The process of claim 8 wherein said nonionic dispersant is an ethylene oxide/propylene oxide block copolymer.

13. The process of claim 8 wherein said wetting agent is sodium dodecyl benzene sulfonate.

14. The process of claim 8 wherein the mole ratio of aluminum oxide to magnesium oxide is 1:1.

15. The process of claim 8 which includes the additional step of spraying water or a binding solution on to the wettable powder formed to produce a desired granule level of hardness, and subsequently drying the treated material to produce a dry flowable formulation.

16. The composition of claim 2 wherein said 1-m-trifluoromethylphenyl-3-chloro-4-chloromethyl-2-pyrrolidone is preconditioned with a polyamide.

* * * * *